United States Patent [19]

Caussignac et al.

[11] Patent Number: 4,497,576
[45] Date of Patent: Feb. 5, 1985

[54] ARTICLE ANALYZER APPARATUS BY SILHOUETTE PROJECTION

[75] Inventors: Jean-Marie Caussignac, Le Perreux sur Marne; Maurice Leroy, Sauteville les Rouen, both of France

[73] Assignee: L'Etat Francais, France

[21] Appl. No.: 338,155

[22] Filed: Jan. 8, 1982

[30] Foreign Application Priority Data

Jan. 14, 1981 [FR] France .................. 81 00549

[51] Int. Cl.³ .............................................. G01N 15/02
[52] U.S. Cl. ................................... 356/335; 250/222.2
[58] Field of Search .................. 356/335, 379, 385; 250/222.2, 560, 571

[56] References Cited

U.S. PATENT DOCUMENTS

| 3,712,469 | 1/1973 | Dwyer et al. | |
| 3,984,154 | 10/1976 | Chin et al. | |
| 4,075,462 | 2/1978 | Rowe | |
| 4,105,925 | 8/1978 | Rossol et al. | 356/379 X |

FOREIGN PATENT DOCUMENTS

| 2413654 | 7/1979 | France | |
| 1479972 | 7/1977 | United Kingdom | 356/335 |
| 2012948 | 8/1979 | United Kingdom | |

OTHER PUBLICATIONS

Pfoutz "Digital Optics for Accurate Gaging", Instruments & Control Systems, vol. 49, No. 11, Nov. 1976, pp. 67-69.
Lehrer "A Fast, Non Contact Approach to Accurate Gauging", Instrument & Control Systems, vol. 49, No. 3, Mar. 1976, pp. 51-57.
Vorobev et al., "Determination of the Particle Composition . . . Contact Free Methods", Stroite'nye Materialy, Moscow, USSR, 1978, No. 7, pp. 17-18.

Primary Examiner—David C. Nelms
Assistant Examiner—Matthew W. Koren
Attorney, Agent, or Firm—Shenier & O'Connor

[57] ABSTRACT

Particle analyzer apparatus using the silhouette projecting method, comprising a fixed laser, a reflecting fixed cylinder of axis orthogonal to the direction of the incident laser beam, and adapted to send back the light towards and through a sheet of particled material, a light receiving device generating signals representative of the light received, means for processing the said signals and display means.

The receiving device may be constituted by a linear array of photodiodes, associated to a system for digitizing the projected silhouettes of the grit particles and for displaying same in the form of a television type image.

Said receiving device may also be constituted by a battery of lenses in the focal point of which are placed analog photoelectrical cells in order to generate signals representative of the covering power of the particles.

3 Claims, 5 Drawing Figures

ARTICLE ANALYZER APPARATUS BY SILHOUETTE PROJECTION

The present invention relates to a particle analyzer apparatus using the silhouette-projecting method, for analyzing a particled material, said apparatus being of the type comprising a fixed laser producing a light beam directed on an optical device adapted to send the light back towards and through a sheet of the material to be examined, falling from a dispensing machine, said apparatus further comprising means for receiving the light which has gone through the sheet of material, said means generating signals which represent the light received, and said apparatus comprising also a signal processing unit and, optionally, means for displaying the signals generated by the receiving means and processed by the processing unit.

Methods and apparatus for contact-free analysis of mixed grit, have recently been developed and are divided into two groups, based respectively on optical diffraction and on silhouette-projection.

This last method consists in examining the silhouettes projected by objects traversing a light beam, mostly for element-counting purposes.

A laser granulometer has also been proposed in an article entitled "Determination of the particle composition of powdered material using contact-free methods by VOROBEV et al (Stroitel'nye materialy, MOSCOW, USSR, 1978, No. 7, pages 17–18).

The apparatus described in the aforecited article comprises a device with rotary mirror producing a scanning light over the sheet of grit. The receiving device is a second rotary mirror synchronous to the first.

The disadvantage with such a device is that it is an apparatus which uses movable mechanical parts, and that it necessitates most of the time, very fine adjustments, hence proving in time unreliable, especially under unfavorable ambient conditions.

It is the object of the present invention to propose a particle analyzer by silhouette-projection which shows none of the aforesaid disadvantages, by, to be more precise, making the device entirely static.

This object is reached according to the invention due to the fact that the optical device is fixed and transforms the laser beam received, into a plane sheet of light extending towards and traversing the sheet of grit at least through its width and from a substantially right angle, before being collected by the receiving device, which receiving device is situated inside the plane of the sheet of light and over a width which corresponds to the width of the sheet of grit.

Advantageously, the optical device is constituted by a reflecting cylinder of axis orthogonal to the direction of the incident laser beam.

According to a first embodiment of the apparatus of the invention, the receiving device is constituted by a linear array of photodiodes each one of which indicates the value 1 or 0, depending on whether or not they receive the light.

Advantageously, the processing device is capable of analyzing the value of the signal delivered by the photodiodes of the array at each time interval $\Delta t$, and to digitize the projected silhouettes of the grit particles, said device comprising read/write memories in which this information is stored and means permitting to display the digitized images of the grit particles in the form of a television-type image.

Advantageously, the apparatus according to the invention further comprises statistical processing means permitting to issue granulometric curves from the information stored in the read/write memories.

According to a second embodiment of the apparatus of the invention, the receiving device is constituted by a battery of lenses in the focal plane of which are placed analog photo-electric cells, in order to generate signals representing the covering power of the particles.

Advantageously, the apparatus comprises, outside the silhouette projected by the sheet of grit, a photo-electrical cell of reference.

The invention also relates to a particle-analyzing method by silhouette-projection which consists in transforming the parallel light beam into a plane sheet of light extending towards and through the sheet of grit over its width at least and from a substantially right angle.

According to a first variant embodiment of the method, the light is picked up on photodiodes which are examined at each time interval $\Delta t$, and the information obtained is stored in read/write memories, to obtain a digitization of the projected silhouettes of the grit particles, which digitization can be displayed, and, advantageously, the digitized silhouettes are statistically processed to obtain granulometric curves.

According to a second variant of embodiment of the method, the light traversing the sheet of grit is picked up on a battery of lenses in the focal point of which are placed analog photoelectrical cells, in order to generate signals representing the covering power of the particles.

The invention will be more readily understood on reading the following description, with reference to the accompanying drawings, in which.

Figure 1:
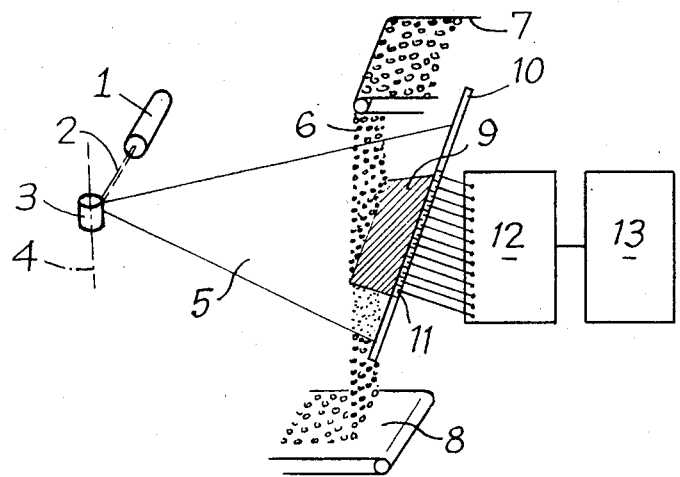
FIG. 1 is a diagrammatical perspective of the first embodiment of an apparatus according to the invention.
Figure 2:
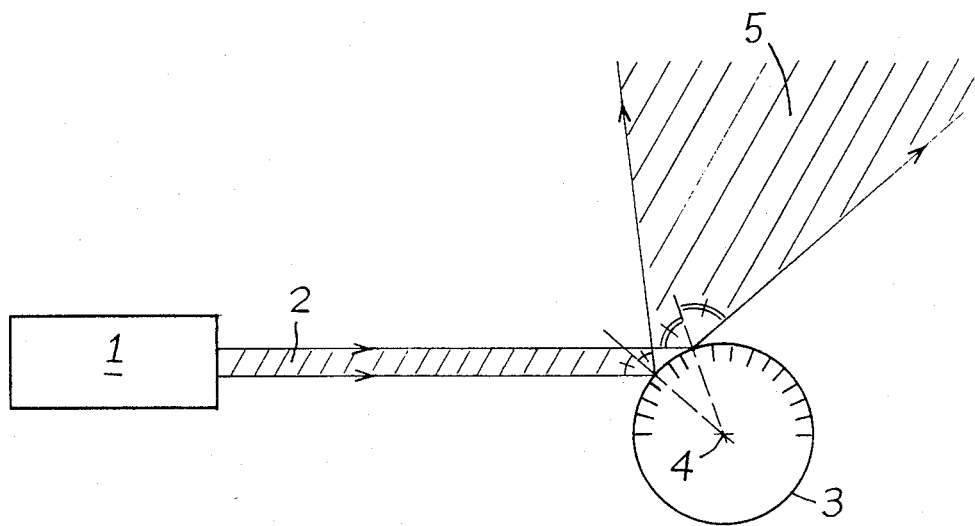
FIG. 2 is a plan view of the optical device according to the invention.

FIG. 1 shows a laser 1 sending a parallel beam of light 2 on to the cylindrical reflecting surface of a cylinder 3 of which the axis 4 is orthogonal to the beam 2 (FIG. 2). The parallel light beam 2 is then reflected, according to nature's law of reflection, as a fan-like divergent beam, forming a sheet of light 5.

Said sheet of light 5, traverses at virtually right angle, a sheet 6 of grit falling from an upper conveyor belt 7 and picked up by a lower conveyor belt 8. The sheet 5 traverses the sheet 6 over at least the width thereof, the angle of opening of said sheet 5 being dependent of the diameter of the cylinder 3.

The silhouette 9 projected by the grit of the sheet 6 is detected by means of a horizontal array 10 (inside the plane of the sheet of light 5) supporting a plurality of adjacent photodiodes 11 over a width which corresponds to the width of the sheet 6 taking into account the divergence of the sheet of light 5.

It is in fact easy to modify, for a given granulometry, the width of the silhouettes projected on the cells by acting on the distances, either between the optical device 3 and the falling plane 6 of the grit, or between the said falling plane 6 and the array 10 of photodiodes.

As regards the photodiodes 11 of the array 10, these can be selected from a wide range of diameters, the choice being dependent on the space available and on their digital processing capacity.

The photodiodes operate in a digital way, i.e. they give a signal of value 1 in the absence of particles and a signal of value 0 in the presence of particles.

A microprocessing system analyzes simultaneously the state of all the cells of the array and stores the resulting information in read/write memories.

Figure 3:
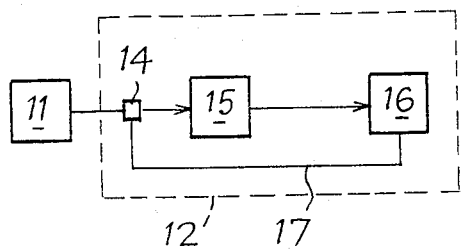
FIG. 3 is a diagrammatical representation of the functioning of the processing device according to the invention.

The processing device 12 comprises an electronic analyzing device of which FIG. 3 illustrates the principle: a photodiode 11 delivers a signal (0 or 1) to a read station 14, said signal is put into the appropriate form by means 15 and stored in a storage register 16, the inquiry loop 17 being produced by a microprocessor.

A display device 13 displays the information recorded in the memories.

Figure 4:
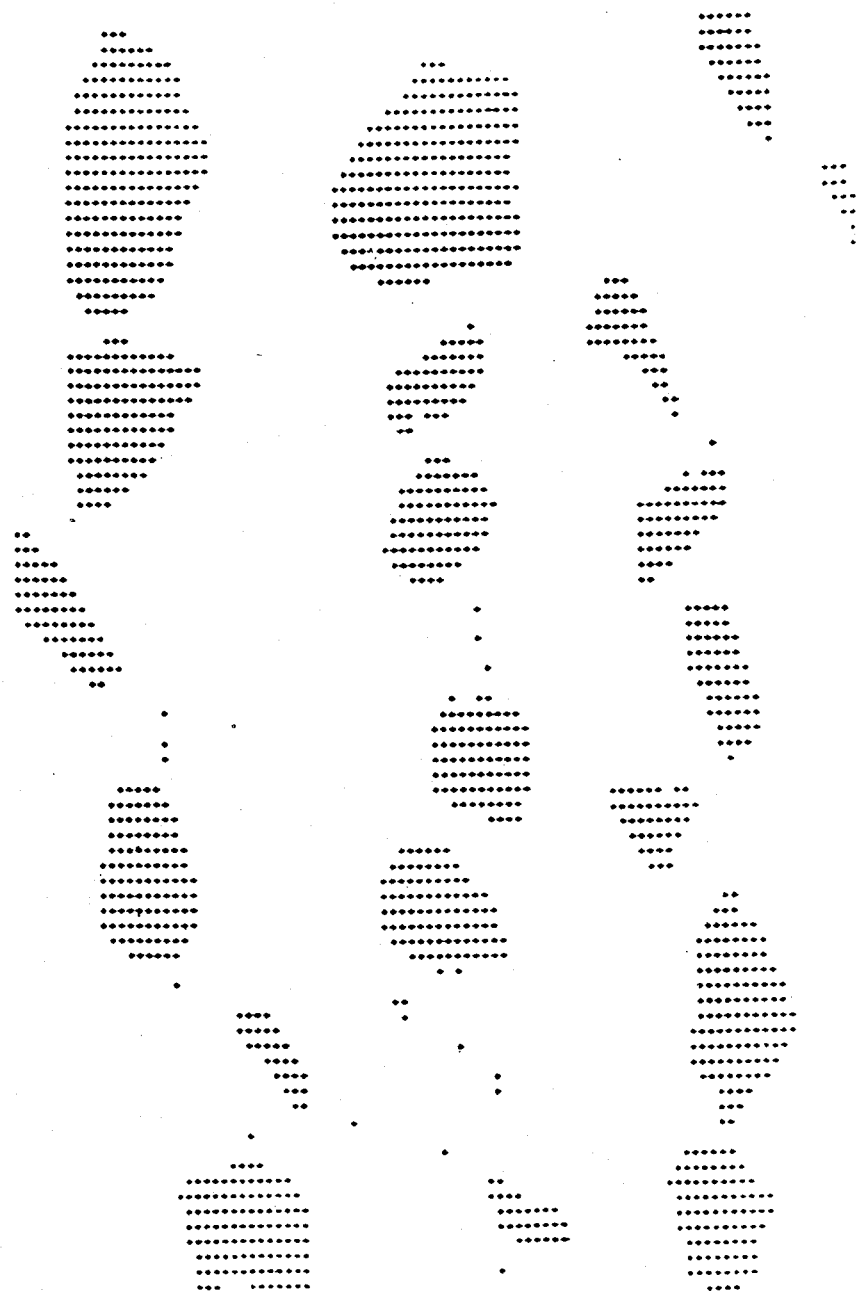
FIG. 4 is a view of the "television type" image representing the digitized projected silhouette of a sample of grit particle obtained with the apparatus shown in FIG. 1.

The digital images of the grit particles are very simply displayed on a printer. At a moment t, the state 0 of a photo-diode (presence of particles) is represented by a cross on the printer, the state 1 (absence of particles) leaves a blank on the paper, thus forming an image substantially comparable to a television image, for each particle (see FIG. 4).

Thereafter, different sub-programs of reduction can classify the resulting images according to criteria of surfaces, of square root of surfaces, of maximum widths, of maximum heights, etc. It goes without saying that the automatic processing of this information is easily effected by well known statistical processing means, the description of which does not fall within the scope of the present invention. But in those cases where the aim is to limit the investment, the "television" type image can be reduced manually, for example on accumulated histograms, to retrieve the normal granulometric curves.

It should right now be noted that the validity of the method proposed is dependent on a more or less accurate verification of a number of assumptions:

(1) All the particles must pass through the sheet of light 5 at the same speed. This assumption is proved to be relatively correct, in view of the low resistance offered by the air, for 2/20 granulometries which are the smallest to which the present method can be applied.

(2) The flow should be in a monolayer form. With small granulometries, it would seem that there is a risk of lumps forming. Therefore, it is necessary, on the one hand, to test perfectly dry particles, and on the other hand, to separate the lumps of particles, by incorporating a vibrating system (not shown) to the means discharging the sheet 6 (upper conveyor belt 7).

(3) The different granulometric classes should be distributed at random, so that the average obturation time for a long enough time interval is identical for all the cells 11.

The limitations of the method come from the sampling pitch which is dependent on the dimension of the detection cells and on the distance between them. The dimension of a cell defines the lower limit of resolution of the projected silhouette of the grit particle which, as already noted, is not necessarily the dimensions of the grit particles.

Depending on the classes of granulometry examined, cells of different diameter may be chosen.

In certain experiments conducted by the Applicant, an array of 32 photodiodes of 1.8 mm diameter was used for particles of small dimensions (<20 mm), and one of 32 cells of 3.6 mm diameter was used for bigger particles (up to 50 mm), in each case the ratio of the distance between the optical device and the sheet of particles, to the distance between said sheet and the cells, being caused to vary. The flow rate selected was about 10 kg/min.

First of all, it was proceeded to gauging the system by means of calibrated balls which were dropped where the grit falling plane 6 is situated. The scanning speed is adjusted so that for a given category of balls, the number of lines which, on the printer output, represents the vertical height of the silhouette of one ball, is identical to the number of points which represents the width of the silhouette of the ball.

A complete series of tests was conducted, after the aforesaid gauging, followed by the plotting of granulometric curves. The granulometric curves obtained with this method are similar to those obtained by the conventional method of sifting.

It was also noted that the adjusting of the granulometric curve was virtually final after only one passage of a sample of particles and that repeated passages did not really improve the accuracy.

The apparatus according to the invention such as shown in FIG. 1, and which has just been described, can therefore be termed to be a contact-free granulometer.

Figure 5:
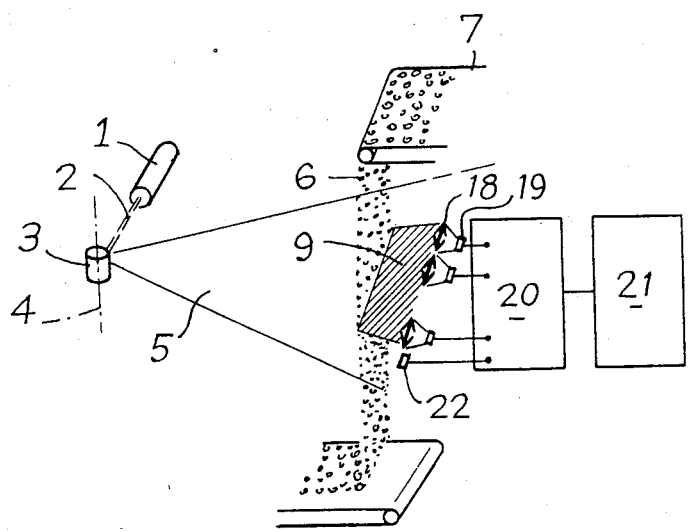
FIG. 5 is a diagrammatical perspective of the second embodiment of an apparatus according to the invention.

A variant of this apparatus, illustrated in FIG. 5, and which is described hereinafter, gives information on the covering power of the particles.

The apparatus comprises, as in the preceding case, a laser 1, an optical device 3 transforming the incident laser beam 2 into a sheet 5 which traverses a sheet 6 of grit. Instead of the array of photodiodes of the granulometer, the apparatus comprises a receiving device constituted by a battery of convergent lenses 18 in the focal point of which are placed analog photoelectrical cells 19, connected to a signal processing device 20 which may be followed by a display device 21.

The width of the lens determines the transverse sampling pitch of the sheet. The pitch adopted in the Applicant's experiments was 50 mm.

Each cell delivers an electrical current which is proportional to the intensity of the light it receives, and therefore to the quantity of light passing through the corresponding sample of sheet. A comparison of the signals of each cell will reveal any heterogeneities there may be.

The analog signals are digitized with a voltage-frequency converter, and are related to the covering power and to the grit flow rate. When selecting a time constant which corresponds to the longitudinal sampling required, the processing device issues a value representative of the covering power on the sample in question.

To remedy any fluctuations of the light beam, a way is made for the reference light outside the silhouette of the sheet of grit, to which way is associated a reference cell 22. Thus it is possible, for each sample, to determine a contrast $\alpha$:

$$\alpha = (I_o(t) - I(t))/I_o(t) \text{ with } I_o(t) = I_o(0) \times I_r(t)/I_r(0)$$

I(t) = quantity of light received by the measuring cell during the time constant $\Delta t$ $I_o(0)$ = quantity of light received by the measuring cell at moment t=0 (absence of grit)

$I_r(t)$ = quantity of light received by the reference cell during time constant $\Delta t$ $I_r(0)$ = quantity of light received by the reference cell at instant t=0 (absence of grit).

Tests conducted with 4/6, 6/10, 14/20 granulometries for flow rates varying between 1.5 and 13 tons/hour for a stream of 100 mm wide, have given percentages varying between a few percent and 75% of the nominal light intensity. In each granulometric class, a linear relation between the contrast and the flow rate (or covering power) was noted, the gradient of the curve varying in relation to the granulometric class considered.

The invention is in no way limited to the description given hereinabove, and on the contrary, covers any modifications that can be brought thereto without departing from its scope.

What is claimed is:

1. Particle analyzing method by silhouette projection consisting in reflecting a parallel light beam issued by a laser toward and through a sheet of particles of a granular material to be examined, in picking up the light which has been through the sheet and in generating signals representative of said light, and processing the said signals in order to obtain information on the particle material, wherein said parallel light beam is transformed into a plane divergent sheet beam of light extending towards and through the sheet of particles over its width at least and from a substantially right angle, said light traversing the sheet of particles being picked up on a battery of lenses in the focal point of which are placed analog photoelectric cells in order to generate signals representing the covering power of the particles.

2. Particle analyzer apparatus for analyzing particles of a granular material by the silhouette projection method, said apparatus including in combination a dispensing machine for forming a sheet of said particles falling with virtually the same speed, a fixed laser for producing a beam of light, an optical device for receiving light from said beam and directing the light back towards and through said sheet of particles, means for receiving light which has passed through the sheet of particles to generate signals representing the light received, and a signal processing unit for processing said signals, said optical device being fixed and transforming the received laser beam into a plane divergent sheet beam of light extending towards and traversing the sheet of particles at least over its width and at a substantially right angle before being collected by the receiving device, said receiving device being situated in the plane of said beam over a width which corresponds to the width of said particles, said optical device being constituted by a reflecting cylinder having an axis orthogonal to the direction of the incident laser beam, said receiving device being constituted by a battery of lenses in the focal plane of which are placed analog photo-electric cells in order to generate signals representing the covering power of the particles.

3. Particle analyzer apparatus as claimed in claim 2, wherein said apparatus comprises, outside the silhouette projected by the sheet of particles, a photoelectrical cell of reference.

* * * * *